US00PP32684P3

(12) United States Plant Patent
Snijder

(10) Patent No.: US PP32,684 P3
(45) Date of Patent: Dec. 22, 2020

(54) ***DAHLIA* PLANT NAMED 'DAHZ0036'**

(50) Latin Name: ***Dahlia* hybrid**
Varietal Denomination: DAHZ0036

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/873,149

(22) Filed: Feb. 13, 2020

(65) Prior Publication Data

US 2020/0337198 P1 Oct. 22, 2020

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 6/144
See application file for complete search history.

(56) References Cited

PUBLICATIONS

UPOV hit to a *Dahlia* plant named, 'DAHZ0036', QZ PBR 2019/0989, filed Apr. 16, 2019.*

* cited by examiner

*Primary Examiner* — Anne Marie Grunberg
(74) *Attorney, Agent, or Firm* — Dale Skalla

(57) ABSTRACT

A new *Dahlia* plant named 'DAHZ0036', particularly distinguished by the large-medium bright scarlet single-type inflorescences, full and medium plant habit with excellent branching, dark-colored foliage and good floriferousness.

1 Drawing Sheet

Latin name of the genus and species of the plant claimed: *Dahlia* hybrid.

Varietal denomination: 'DAHZ0036'.

BACKGROUND OF THE NEW PLANT

The present invention comprises a new *Dahlia*, botanically known as *Dahlia* hybrid and hereinafter referred to by the variety name 'DAHZ0036'.

'DAHZ0036' is a product of a planned breeding program. The new cultivar 'DAHZ0036' has large-medium bright scarlet single-type inflorescences, full and medium plant habit with excellent branching, dark-colored foliage and good floriferousness.

'DAHZ0036' originated from an open pollination made in Lisse, The Netherlands. The pollination took place in August 2014 and all the seeds were harvested together without knowing seed source. Seed was sown in January 2015. 'DAHZ0036' was selected as one flowering plant within the progeny of the stated cross in May 2015 in a controlled environment in Lisse, The Netherlands.

The female and male parents of 'DAHZ0036' are unknown.

The first act of asexual reproduction of 'DAHZ0036' was accomplished when vegetative stem cuttings were propagated from the initial selection in May 2015 in a controlled environment in Lisse, The Netherlands.

Horticultural examination of plants grown from cuttings of the plant initiated in May 2015 in Lisse, The Netherlands, and continuing thereafter, has demonstrated that the combination of characteristics as herein disclosed for 'DAHZ0036' are firmly fixed and are retained through successive generations of asexual reproduction.

'DAHZ0036' has not been observed under all possible environmental conditions. The phenotype may vary significantly with variations in environment such as temperature, light intensity and day length.

BRIEF DESCRIPTION OF THE PHOTOGRAPHS

Figure 1:
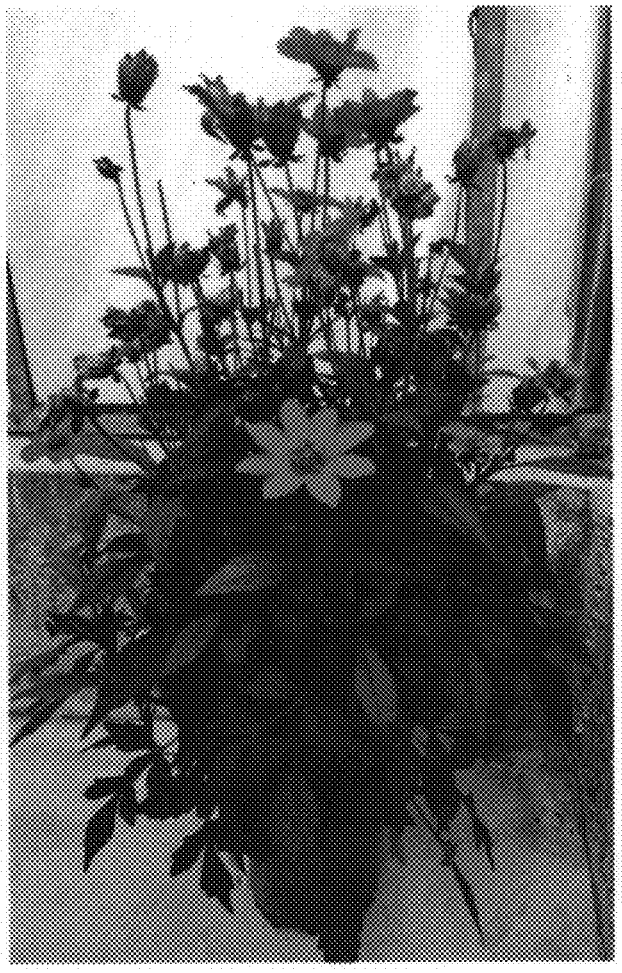
Figure 2:
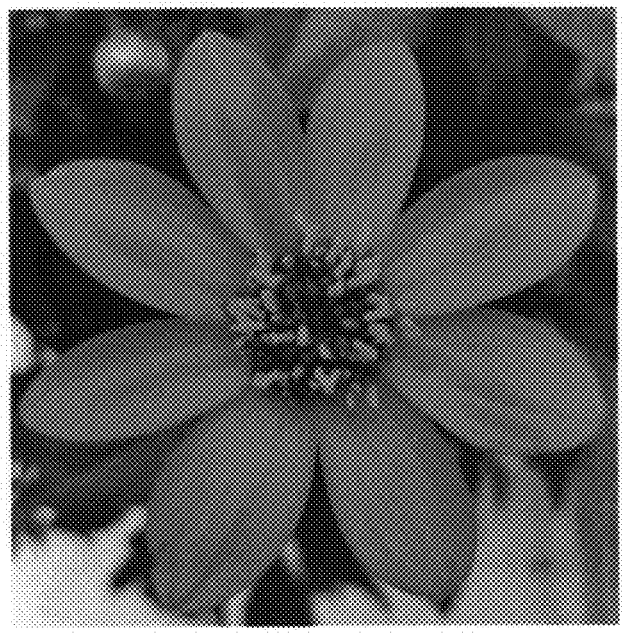

The accompanying photographic drawings show typical flower and foliage characteristics of 'DAHZ0036' with colors being as true as possible with an illustration of this type. The photographic drawings show in FIG. 1, a flowering potted plant of the new variety and in FIG. 2, a close-up of the flowers.

DETAILED BOTANICAL DESCRIPTION

The plant descriptions and measurements were taken in Andijk, The Netherlands in week 32 on plants that were growing in 55 cm pots in an outside trial and were about 20 weeks old. The aforementioned whole plant photograph was taken in week 31 and the flower close-up was taken in week 31, both in Enkhuizen, The Netherlands. The plants were grown in 19 cm pots in the greenhouse and were about 20 weeks of age.

A Plant Breeder's Right for this cultivar was applied for in the European Union on Apr. 16, 2019, No. 2019/0989. 'DAHZ0036' has not been made publicly available prior to the effective filing date of this application, notwithstanding any disclosure that may have been made less than one year prior to the effective filing date of this application by the inventor or another who obtained 'DAHZ0036' directly from the inventor.

Color references are made to The Royal Horticultural Society Colour Chart (R.H.S.) 2001.

BRIEF SUMMARY OF INVENTION

The following traits have been repeatedly observed and are determined to be basic characteristics of the new variety. The combination of these characteristics distinguishes this *Dahlia* as a new and distinct variety.

TABLE 1

DIFFERENCES BETWEEN THE NEW VARIETY 'DAHZ0036' AND A SIMILAR VARIETY

| | 'DAHZ0036' | 'HDSC18' (U.S. Plant Pat. No. 26,962) |
|---|---|---|
| Ligulate flower color: | RHS 33A | RHS 46A |
| Tubular flower color: | RHS 46A | RHS 21A |
| Plant height: | 55 cm | 30 cm |

Plant:

*Form, growth and habit.*—Inverted triangular plant form; relatively compact and mounding plant habit; suitable as container and garden plants; freely basal branching dense and bushy appearance.

*Plant height.*—50-55 cm.

*Plant height (inflorescence included).*—50-55 cm.

*Plant width.*—About 30 cm.

*Garden performance and tolerance to weather.*—Good.

*Crop time to flowering.*—About 65 days after planting.

Roots:

*Number of days to initiate and develop roots.*—About 12-15 days at about 21 degrees C.

*Type.*—Fine, fibrous, free branching.

*Color.*—Typically white to brown.

Foliage:

*Arrangement.*—Opposite, simple or compound with three or five leaflets per leaf.

*Immature, leaf color, upper surface.*—Close to RHS N199A.

*Lower surface.*—Close to RHS 191A.

*Mature, leaf color, upper surface.*—Darker than RHS 147A.

*Lower surface.*—RHS 191B but slightly more greyish.

*Length.*—7-15 cm.

*Width.*—3-8 cm.

*Shape.*—Ovate.

*Base shape.*—Attenuate.

*Apex shape.*—Acuminate.

*Margin.*—Crenate.

*Texture, upper surface.*—Glabrous, slightly glossy.

*Lower surface.*—Glabrous.

*Venation color, upper.*—RHS 146B.

*Lower.*—RHS 191A.

*Petiole color.*—RHS 146A.

*Petiole length.*—About 1.8 cm.

*Diameter of petiole.*—0.3 cm at the mid section.

*Texture.*—Glabrous.

Stem:

*Average quantity of main branches per plant.*—About 6-10.

*Color of stem.*—Close to RHS 148A; distally tinged with close to RHS N199A.

*Length of stem.*—5-10 cm.

*Diameter.*—0.4-1 cm at the midsection.

*Length of internodes.*—About 3 cm to 12 cm.

*Texture.*—Glabrous.

*Color of peduncle.*—Close to RHS 200A.

*Length of peduncle.*—12 cm.

*Peduncle diameter.*—0.2-0.3 cm.

*Texture.*—Glabrous.

Inflorescence:

*Type.*—Single-type inflorescences positioned above and beyond the foliar plane on strong peduncles.

*Blooming habit.*—Continuous throughout the growing season.

*Average quantity of inflorescences per plant.*—About 50 inflorescences.

*Average quantity of inflorescences per lateral stem.*—2-3.

*Lastingness of individual blooms on the plant.*—About 12 days.

*Fragrance.*—None.

Bud (just before opening):

*Color.*—Close to RHS 187B.

*Length.*—1.6 cm.

*Width.*—1.3 cm.

*Shape.*—Oblate to close to globular.

Immature inflorescence:

*Diameter.*—About 6 cm.

*Color of ray florets, upper surface.*—RHS 4A.

*Lower surface.*—RHS 2B.

Mature inflorescence:

*Diameter.*—About 9.5 cm.

*Depth.*—1.7-1.8 cm.

*Total diameter of 'disc'.*—1.5-1.8 cm.

*Recepticle height.*—0.7-0.8 cm.

*Recepticle diameter.*—1.3-1.4 cm.

Ray florets:

*Average quantity of florets.*—About 8.

*Color of florets, upper surface.*—RHS 33A.

*Lower surface.*—RHS 34A.

*Length.*—3.7-4.0 cm.

*Width.*—2.2-2.6 cm.

*Shape.*—Broadly elliptical.

*Base shape.*—Attenuate.

*Apex shape.*—Mucronulate.

*Margin.*—Entire.

*Texture, upper surface.*—Smooth, glabrous, shiny.

*Lower surface.*—Smooth, glabrous, matte.

Disc florets:

*Average quantity of florets.*—About 85 arranged in about 17 whorls.

*Color of florets.*—RHS 46A.

*Length.*—0.6-0.7 cm.

*Diameter.*—0.08 cm.

*Shape.*—Tubular.

*Apex shape.*—Dentate, 5-pointed.

Phyllaries:

*Average quantity.*—About five arranged in a single whorl.

*Color, upper surface.*—Close to RHS 200A.

*Lower surface.*—Close to RHS 200A.

*Length.*—1.3-1.5 cm.

*Width.*—0.4-0.6 cm.

*Shape.*—Ovate to lanceolate.

*Base shape*.—Attenuate.
*Apex shape*.—Acuminate.
*Margins*.—Entire.
*Texture, upper surface*.—Smooth, glabrous, glossy.
*Lower surface*.—Smooth, glabrous, glossy.

Reproductive organs:

*Gyneocium*.—Present on disc florets only.
*Pistil quantity*.—1 per floret.
*Length*.—0.6-0.8 cm.
*Style color*.—RHS 154D.
*Style length*.—0.5-0.6 cm.
*Stigma color*.—Close to RHS 12B.
*Stigma shape*.—Bi-furchate (bi-lobed).
*Ovary color*.—RHS 145C.
*Andreocium*.—Present on disc florets only.
*Stamens quantity*.—5 united.
*Color of filaments*.—RHS 2C.
*Length filaments*.—0.4 cm.
*Anther color*.—Close to RHS 16A.
*Anther length*.—0.2-0.4 cm.
*Color of pollen*.—RHS 23A.
*Pollen amount*.—Abundant.
*Fertility/seed set*.—Not observed on this hybrid.

Disease/pest resistance: Disease resistance or susceptibility has not been observed on this hybrid.

What is claimed is:

1. A new and distinct variety of *Dahlia* plant named 'DAHZ0036', substantially as illustrated and described herein.

* * * * *